United States Patent
Pepin et al.

(10) Patent No.: US 12,070,604 B2
(45) Date of Patent: *Aug. 27, 2024

(54) OPTIMIZING NEUROMODULATION STIMULATION PARAMETERS USING BLOOD PARAMETER SENSING

(71) Applicant: Galvani Bioelectronics Limited, Brentford (GB)

(72) Inventors: Brian Pepin, South San Francisco, CA (US); Shiv Sabesan, South San Francisco, CA (US)

(73) Assignee: GALVANI BIOELECTRONICS LIMITED, Stevenage (GB)

(*) Notice: Subject to any disclaimer, the term of this patent is extended or adjusted under 35 U.S.C. 154(b) by 392 days.

This patent is subject to a terminal disclaimer.

(21) Appl. No.: 17/450,308

(22) Filed: Oct. 8, 2021

(65) Prior Publication Data

US 2022/0023635 A1 Jan. 27, 2022

Related U.S. Application Data

(63) Continuation of application No. 16/485,673, filed as application No. PCT/US2018/017831 on Feb. 12, 2018, now Pat. No. 11,167,143.

(Continued)

(51) Int. Cl.
*A61N 1/36* (2006.01)
*A61N 1/05* (2006.01)
*A61N 1/375* (2006.01)

(52) U.S. Cl.
CPC ....... *A61N 1/36139* (2013.01); *A61N 1/0534* (2013.01); *A61N 1/36007* (2013.01);
(Continued)

(58) Field of Classification Search
CPC .............. A61N 1/0534; A61N 1/36007; A61N 1/36031; A61N 1/36062; A61N 1/36064;
(Continued)

(56) References Cited

U.S. PATENT DOCUMENTS

| | | | | |
|---|---|---|---|---|
| 2006/0116737 A1* | 6/2006 | Libbus | ............... | A61N 1/37264 607/44 |
| 2006/0129204 A1* | 6/2006 | Pless | ...................... | A61B 5/372 607/45 |

(Continued)

FOREIGN PATENT DOCUMENTS

| | | |
|---|---|---|
| WO | 2015103512 | 7/2015 |
| WO | 2016127130 | 8/2016 |
| WO | 2016128985 | 8/2016 |

OTHER PUBLICATIONS

International Search Report and Written Opinion, Application No. PCT/US2018/017831, dated May 24, 2018, 10 pages.

(Continued)

*Primary Examiner* — George Manuel
(74) *Attorney, Agent, or Firm* — Merchant & Gould P.C.

(57) ABSTRACT

This disclosure relates to implantable neuromodulation systems and methods, and in particular to systems and methods for sensing blood-based parameter changes triggered by neural stimulation and subsequently optimizing the stimulation parameters based on feedback from the sensed blood-based parameter changes. Embodiments are directed to a method that includes delivering neural stimulation to a nerve or artery/nerve plexus based on a first set of stimulation parameters, monitoring a response to the neural stimulation that includes monitoring responses of the nerve or artery/nerve plexus and blood-based parameters of the artery, modifying the first set of the stimulation parameters based on the blood-based parameters to create a second set of (Continued)

stimulation parameters, and delivering the neural stimulation based on the second set of the stimulation parameters.

17 Claims, 5 Drawing Sheets

Related U.S. Application Data

(60) Provisional application No. 62/458,757, filed on Feb. 14, 2017.

(52) U.S. Cl.
CPC ..... *A61N 1/36031* (2017.08); *A61N 1/36067* (2013.01); *A61N 1/36135* (2013.01); *A61N 1/3614* (2017.08); *A61N 1/36171* (2013.01); *A61N 1/36175* (2013.01); *A61N 1/36062* (2017.08); *A61N 1/36064* (2013.01); *A61N 1/36071* (2013.01); *A61N 1/36085* (2013.01); *A61N 1/36096* (2013.01); *A61N 1/3752* (2013.01)

(58) Field of Classification Search
CPC ............ A61N 1/36067; A61N 1/36071; A61N 1/36085; A61N 1/36096; A61N 1/36135; A61N 1/36139; A61N 1/3614; A61N 1/36171; A61N 1/36175; A61N 1/3752
See application file for complete search history.

(56) References Cited

U.S. PATENT DOCUMENTS

| | | |
|---|---|---|
| 2007/0142864 A1 | 6/2007 | Libbus |
| 2009/0012375 A1 | 1/2009 | Pitsillides |
| 2009/0192566 A1 | 7/2009 | Ng |
| 2013/0053924 A1 | 2/2013 | Libbus |
| 2014/0046407 A1* | 2/2014 | Ben-Ezra ........... A61N 1/36053 607/72 |
| 2014/0135886 A1* | 5/2014 | Cook ................ A61N 1/36025 607/136 |

OTHER PUBLICATIONS

International Preliminary Report on Patentability, Application No. PCT/US2018/017831, dated Aug. 20, 2018, 7 pages.

* cited by examiner

OPTIMIZING NEUROMODULATION STIMULATION PARAMETERS USING BLOOD PARAMETER SENSING

PRIORITY CLAIM

This application is a continuation of application Ser. No. 16/485,673 filed Aug. 13, 2019, which in turn is a National Phase entry of PCT Application No. PCT/US18/17831, filed Feb. 12, 2018, which claims priority from U.S. Provisional Application No. 62/458,757, filed Feb. 14, 2017, which is hereby fully incorporated herein by reference.

TECHNICAL FIELD

The present disclosure relates to implantable neuromodulation systems and methods, and in particular to systems and methods for sensing blood-based parameter changes triggered by neural stimulation and subsequently optimizing the stimulation parameters based on feedback from the sensed blood-based parameter changes.

BACKGROUND

Normal neural activity is an intricate balance of electrical and chemical signals which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Rheumatoid arthritis is an autoimmune disorder that occurs when the immune system mistakenly attacks body's own tissues. Unlike the wear and tear damage (due to age and/or extreme sports) of osteoarthritis, rheumatoid arthritis affects the lining of the joints, causing a painful swelling that can eventually result in bone erosion and joint deformity. The inflammation associated with rheumatoid arthritis is what can damage other parts of the body as well. While new types of medications have improved treatment options dramatically, severe rheumatoid arthritis can still cause physical disabilities. Recently, neuromodulation has been suggested as a potential treatment option for patients suffering from rheumatoid arthritis. Specifically, electrical stimulation of the vagus nerve has shown promise. However, since the vagus nerve is a heterogeneous bundle of nerve fibers, stimulation of the vagus nerve may cause inadvertent stimulation of other end-organs resulting in adverse side effects. From this perspective, the direct stimulation of the end-organ may have a higher probability of being more treatment-specific while avoiding or minimizing the adverse physiological effects.

In rheumatoid arthritis, this implies that stimulation of the splenic artery or the splenic artery/nerve plexus (close to the end-organ) to innervate the spleen may control inflammation while avoiding or minimizing the adverse side effects. A major challenge of stimulating a nerve or artery/nerve plexus is to ensure that optimal stimulation parameters are identified that maximally control inflammation while avoiding or minimizing any influence on the functioning of peripheral organs such as blood flow via the artery. Therefore, the ability to measure stimulus evoked blood parameter changes locally, for example, measuring blood oxygenation, blood flow, arterial distension, and blood pressure at the artery, is important for the success of the neuromodulation system. Furthermore, optimizing neural stimulation parameters and identifying the subset of parameters that may cause the inadvertent side effects is important from a safety perspective. Accordingly, the need exists for neuromodulation systems and methods that have the capability to optimize neuromodulation stimulation parameters based on feedback from stimulus evoked blood parameter changes.

BRIEF SUMMARY

In various embodiments, a medical device is provided that comprises a controller configured to provide a first set of stimulation parameters, and a pulse generator configured to generate neural stimulation based on the first set of stimulation parameters. The medical device further comprises a lead body, including a conductor material connected to the electronics module, one or more stimulation electrodes connected to the conductor material and configured to deliver the neural stimulation generated by the pulse generator to a nerve or artery/nerve plexus, one or more recording electrodes connected to the conductor material and configured to: monitor a response to the neural stimulation that includes electrical impulses traveling through the nerve or artery/nerve plexus, and send information regarding the electrical impulses to the controller via the conductive material, and one or more sensors connected to the conductor material and configured to: monitor the response to the neural stimulation that includes blood-based parameters, and send the blood-based parameters to the controller via the conductive material. The controller is further configured to modify the first set of the stimulation parameters based on the blood-based parameters to create a second set of stimulation parameters, the pulse generator is further configured to generate modified neural stimulation based on the second set of stimulation parameters, and the one or more stimulation electrodes are further configured to deliver the modified neural stimulation to the nerve or artery/nerve plexus.

In other embodiments, a medical device is provided that comprises an implantable neurostimulator, including a housing, a feedthrough assembly that passes through the housing, and an electronics module within the housing and connected to the one or more feedthroughs. The electronics module includes a pulse generator, a controller, and a memory storing program instructions. The medical device further comprises a lead assembly including a lead body including a conductor material, a lead connector that connects the conductor material to the feedthrough assembly, and one or more electrodes and one or more sensors connected to the conductor material. The program instructions, when operated on by the controller, cause the controller to perform operations comprising delivering neural stimulation using the pulse generator and the one or more electrodes based on a first set of stimulation parameters to a nerve or artery/nerve plexus, monitoring a response to the neural stimulation that includes monitoring responses of the nerve or artery/nerve plexus and blood-based parameters of the artery using the one or more sensors, modifying the first set of the stimulation parameters based on the blood-based parameters to create a second set of stimulation parameters, and delivering the neural stimulation using the pulse generator and the one or more electrodes based on the second set of the stimulation parameters.

In accordance with some aspects, the stimulation parameters include at least one of: stimulation amplitude, pulse width, frequency, duty cycle, stimulation waveform shape, and electrode configuration. Optionally, the blood-based parameters include at least one of blood flow, blood pressure, and arterial distension, and the one or more sensors include at least one of: a blood flow sensor, a blood pressure sensor, and a distension sensor.

In accordance with some aspects, the one or more sensors include at least one of: a blood flow sensor, a blood pressure sensor, and a distension sensor. Optionally, the blood flow sensor is a Doppler sensor configured to measure blood velocity. Optionally, the blood flow sensor is an impedance sensor configured to detect changes in electrical impedance of blood. Optionally, the blood pressure sensor is an impedance sensor configured to measure the blood pressure. Optionally, the blood pressure sensor is a piezoresistive pressure sensor configured to measure the blood pressure. Optionally, the arterial distension sensor is a capacitive sensor configured to measure the arterial distension. Optionally, the arterial distension sensor is a photonic sensor configured to measure arterial distension based on a change in an amount of photons transmitted. Optionally, the arterial distension sensor is a Doppler sensor configured to measure cardiac motion and artery diameter pulsation.

In various embodiments, a medical system is provided for that includes one or more processors and a memory coupled to the one or more processors. The memory is encoded with a set of instructions configured to perform a process comprising delivering, using one or more stimulation electrodes, neural stimulation to a nerve or artery/nerve plexus based on a first set of stimulation parameters, monitoring a response to the neural stimulation that includes monitoring, using one or more recording electrodes, responses of the nerve or artery/nerve plexus and monitoring, using one or more sensors, blood-based parameters of the artery, modifying, using the one or more processors, the first set of the stimulation parameters based on the blood-based parameters to create a second set of stimulation parameters, and delivering, using the one or more stimulation electrodes, the neural stimulation to the nerve or artery/nerve plexus based on the second set of the stimulation parameters.

In accordance with some aspects, the stimulation parameters include at least one of: stimulation amplitude, pulse width, frequency, duty cycle, stimulation waveform shape, and electrode configuration. Optionally, the blood-based parameters include at least one of blood flow, blood pressure, and arterial distension, and the one or more sensors include at least one of: a blood flow sensor, a blood pressure sensor, and a distension sensor.

In accordance with some aspects, the one or more sensors include at least one of: a blood flow sensor, a blood pressure sensor, and a distension sensor. Optionally, the blood flow sensor is a Doppler sensor configured to measure blood velocity. Optionally, the blood flow sensor is an impedance sensor configured to detect changes in electrical impedance of blood. Optionally, the blood pressure sensor is an impedance sensor configured to measure the blood pressure. Optionally, the blood pressure sensor is a piezoresistive pressure sensor configured to measure the blood pressure. Optionally, the arterial distension sensor is a capacitive sensor configured to measure the arterial distension. Optionally, the arterial distension sensor is a photonic sensor configured to measure arterial distension based on a change in an amount of photons transmitted. Optionally, the arterial distension sensor is a Doppler sensor configured to measure cardiac motion and artery diameter pulsation.

In accordance with some aspects, the monitoring of the response to the neural stimulation includes determining whether the neural stimulation has a physiological effect. Optionally, in determining whether the neural stimulation has the physiological effect, the process includes obtaining blood-based parameters and comparing the blood-based parameters to one or more predetermined thresholds to determine whether the neural stimulation has an adverse physiological effect on the blood-based parameters. In certain embodiments, when the neural stimulation has an adverse physiological effect, the first set of the stimulation parameters are modified based on the blood-based parameters to create the second set of stimulation parameters.

In accordance with some aspects, the process further comprises modifying the first set of the stimulation parameters based on a titration schedule and the blood-based parameters to create the second set of stimulation parameters. Optionally, the process further includes determining whether adequate adaptation is achieved. In certain embodiments, the adequate adaptation is achieved when at least one of the following objectives is achieved: acceptable levels for the blood-based parameters, a target intensity level for one or more of the stimulation parameters, and a target physiological effect. When the adequate adaptation is not achieved, the first set of the stimulation parameters are modified based on the titration schedule and the blood-based parameters to create the second set of stimulation parameters.

In various embodiments, a method is provided for that provides neurostimulation. The method includes delivering, by a computing system, neural stimulation to a nerve or artery/nerve plexus based on a first set of stimulation parameters, monitoring, by the computing system, a response to the neural stimulation that includes monitoring responses of the nerve or artery/nerve plexus and blood-based parameters of the artery, modifying, by the computing system, the first set of the stimulation parameters based on the blood-based parameters to create a second set of stimulation parameters, and delivering, by the computing system, the neural stimulation based on the second set of the stimulation parameters.

In accordance with some aspects, the blood-based parameters include at least one of blood flow, blood pressure, and arterial distension. In some embodiments, the monitoring the response to the neural stimulation includes determining whether the neural stimulation has a physiological effect. In some embodiments, the determining whether the neural stimulation has the physiological effect includes obtaining the blood-based parameters and comparing the blood-based parameters to one or more predetermined thresholds to determine whether the neural stimulation has an adverse physiological effect on the blood-based parameters. In certain embodiments, when the neural stimulation has the adverse physiological effect, the first set of the stimulation parameters is modified based on the blood-based parameters to create the second set of stimulation parameters.

In accordance with some aspects, the method further includes modifying the first set of the stimulation parameters based on a titration schedule and the blood-based parameters to create the second set of stimulation parameters. In some embodiments, the method further includes determining whether adequate adaptation is achieved. In certain embodiments, the adequate adaptation is achieved when at least one of the following objectives is achieved: acceptable levels for the blood-based parameters, a target intensity level for one or more of the stimulation parameters, and a target physiological effect. When the adequate adaptation is not achieved, the first set of the stimulation parameters is modified based on the titration schedule and the blood-based parameters to create the second set of stimulation parameters.

In accordance with some aspects, the monitoring of the response to the neural stimulation includes determining whether the neural stimulation has a physiological effect. Optionally, the determination of whether the neural stimulation has the physiological effect includes obtaining the blood-based parameters and comparing the blood-based parameters to one or more predetermined thresholds to determine whether the neural stimulation has an adverse physiological effect on the blood-based parameters. In various embodiments, when the neural stimulation has the adverse physiological effect, the first set of the stimulation parameters is modified based on the blood-based parameters to create the second set of stimulation parameters.

In accordance with some aspects, the method further includes modifying the first set of the stimulation parameters based on a titration schedule and the blood-based parameters to create the second set of stimulation parameters. Optionally, the method further includes determining whether adequate adaptation is achieved. The adequate adaptation may be achieved when at least one of the following objectives is achieved: acceptable levels for the blood-based parameters, a target intensity level for one or more of the stimulation parameters, and a target physiological effect. In various embodiments, when adequate adaptation is not achieved, the first set of the stimulation parameters is modified based on the titration schedule and the blood-based parameters to create the second set of stimulation parameters.

In various embodiments, a non-transitory computer readable storage medium is provide for that stores instructions that, when executed by one or more processors of computing system, cause the computing system to perform operations including delivering neural stimulation to a nerve or artery/nerve plexus based on a first set of stimulation parameters, monitoring a response to the neural stimulation that includes monitoring responses of the nerve or artery/nerve plexus and blood-based parameters of the artery, modifying the first set of the stimulation parameters based on the blood-based parameters to create a second set of stimulation parameters, and delivering the neural stimulation based on the second set of the stimulation parameters.

In accordance with some aspects, the monitoring of the response to the neural stimulation includes determining whether the neural stimulation has a physiological effect. Optionally, the determination of whether the neural stimulation has the physiological effect includes obtaining the blood-based parameters and comparing the blood-based parameters to one or more predetermined thresholds to determine whether the neural stimulation has an adverse physiological effect on the blood-based parameters. In various embodiments, when the neural stimulation has the adverse physiological effect, the first set of the stimulation parameters is modified based on the blood-based parameters to create the second set of stimulation parameters.

In accordance with some aspects, the operations further include modifying the first set of the stimulation parameters based on a titration schedule and the blood-based parameters to create the second set of stimulation parameters. Optionally, the operations further include determining whether adequate adaptation is achieved. Adequate adaptation is achieved when at least one of the following objectives is achieved: acceptable levels for the blood-based parameters, a target intensity level for one or more of the stimulation parameters, and a target physiological effect. In various embodiments, when adequate adaptation is not achieved, the first set of the stimulation parameters is modified based on the titration schedule and the blood-based parameters to create the second set of stimulation parameters.

In various embodiments, a system is provided for that includes a neurostimulator configured to deliver stimulation for a nerve or artery/nerve plexus based on a first set of stimulation parameters, one or more sensors configured to monitor a response to the stimulation that includes monitoring responses of the nerve or artery/nerve plexus and blood-based parameters of the artery, and a controller configured to modify the first set of the stimulation parameters based on the blood-based parameters to create a second set of stimulation parameters. The neurostimulator is further configured to deliver the stimulation based on the second set of the stimulation parameters.

In accordance with some aspects, the neurostimulator, the one or more sensors, and the controller are provided within a distributed environment, and at least the neurostimulator and the controller are in communication via a wireless communication network.

In accordance with other aspects, the neurostimulator, the one or more sensors, and the controller are provided within a distributed environment, and at least the neurostimulator and the one or more sensors are in communication via a wireless communication network.

In various embodiments, a medical system is provided for that includes one or more processors and a memory coupled to the one or more processors. The memory is encoded with a set of instructions configured to perform a process comprising delivering, using one or more stimulation electrodes, neural stimulation to a nerve or artery/nerve plexus based on a first set of stimulation parameters, monitoring a response to the neural stimulation that includes monitoring, using one or more recording electrodes, responses of the nerve or artery/nerve plexus and modifying, using the one or more processors, the first set of the stimulation parameters based on the responses of the nerve or artery/nerve plexus and the blood-based parameters to create a second set of stimulation parameters, and delivering, using the one or more stimulation electrodes, the neural stimulation to the nerve or artery/nerve plexus based on the second set of the stimulation parameters.

BRIEF DESCRIPTION OF THE DRAWINGS

The present disclosure will be better understood in view of the following non-limiting figures, in which.

DETAILED DESCRIPTION

I. Introduction

Figure 1:
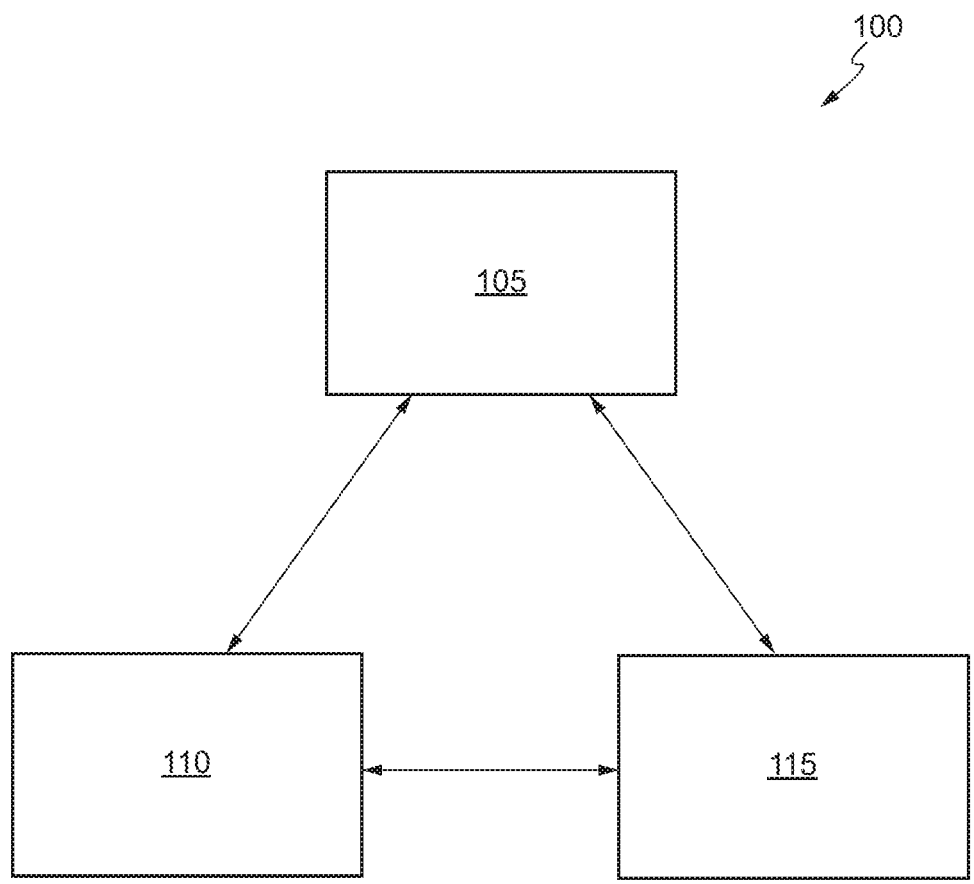
FIG. 1 shows an shows a neuromodulation system in accordance with some aspects of the present disclosure.

The following disclosure describes neuromodulation systems and methods for affecting neural stimulation efficiency and/or efficacy. Various embodiments of systems and/or methods described herein may be directed toward controlling, adjusting, modifying, and/or varying one or more manners in which neural stimulation may be applied or delivered to a patient, thereby possibly 1) influencing, affecting, maintaining, or improving neural stimulation efficacy; and/or 2) influencing, affecting, maintaining, improving, minimizing, or preventing physiological effects caused by the neural stimulation. As used herein, neuromodulation means the alteration of nerve activity through targeted delivery of a stimulus, such as electrical stimulation or chemical agents, to specific neurological sites in the body. A neurostimulator is a device or system having electronic circuit components and/or software configured to deliver the stimulus to the specific neurological site (e.g., a nerve or artery/nerve plexus) via an electrode assembly. One or more portions of the neurostimulator may be implanted in a patient's body. For example, an implanted pulse generator may be encased in a hermetically sealed housing and surgically implanted in a patient. The electrode assembly may be included as a portion of the housing or provided in a separate location and attached to the pulse generator via one or more leads. The stimulus, stimulation, or neural stimulation may comprise electrical, chemical, optical, ultrasonic, and/or magnetic stimulation signals, and may be defined in accordance with spatial, temporal, electrical, and/or magnetic signal parameters, properties, and/or characteristics. The neural stimulation is generally delivered or applied to the patient in accordance with a treatment protocol. Typically, the treatment protocol specifies an optimal or best set of parameters directed toward maximally alleviating one or more patient symptoms through neural stimulation applied in a continuous, generally continuous, or nearly continuous manner.

In various embodiments, the present disclosure is directed to a neuromodulation device or system including a neurostimulator to deliver stimulation to a nerve or artery/nerve plexus, one or more sensors to sense physiological responses to the stimulation, and a controller to control parameters of the stimulation based on physiological responses. A technological problem associated with conventional neuromodulation devices and systems, however, is that they do not have the ability to sense both the physiological responses of the nerve or artery/nerve plexus to the stimulation and blood-based parameter changes of the artery, nor provide adjustment of the stimulation parameters based on the physiological responses of the nerve or artery/nerve plexus, changes in the blood-based parameters, or a combination thereof. These systems and approaches are both inefficient in effectiveness and unreasonably risky with respect to potential for neural damage and resulting physiological effects.

To address these technological problems, the present disclosure is directed to neuromodulation devices or systems that have a neural interface comprising one or more contacts or sensors that can be used to monitor nerve responses and measure at least one of: blood flow, blood pressure, and arterial distension. The monitored nerve response and measurement of blood flow, blood pressure, and/or arterial distension can then be used by the neuromodulation devices or systems to determine whether a patient is experiencing a physiological effect due to the neural stimulation (e.g., an adverse physiological effect such as decreased blood flow along with increased arterial distension may suggest decreases in oxygenation in the blood that may be caused due to an occlusion in the artery as a result of the neural stimulation). In some embodiments, the neuromodulation devices or systems provide on-demand neuromodulation therapy using a closed control system or closed-loop system (feedback control) where an open loop system is used as the forward path but one or more feedback loops or paths are included between the output signal and the input signal. For example, the modification of stimulation parameters and subsequent burst or periodic release of neural stimulation from one or more electrodes can be triggered based on an electrical recording from one or more recording electrodes and/or a measurement of blood flow, blood pressure, and/or arterial distension from one or more sensors. As used herein, when an action is "triggered by" or "based on" something, this means the action is triggered or based at least in part on at least a part of the something.

One illustrative embodiment of the present disclosure comprises a medical system including one or more processors and a memory coupled to the one or more processors. The memory is encoded with a set of instructions configured to perform a process comprising delivering, using one or more stimulation electrodes, neural stimulation to a nerve or artery/nerve plexus based on a first set of stimulation parameters, monitoring a response to the neural stimulation that includes monitoring, using one or more recording electrodes, responses of the nerve or artery/nerve plexus and monitoring, using one or more sensors, blood-based parameters of the artery, modifying, using the one or more processors, the first set of the stimulation parameters based on the blood-based parameters to create a second set of stimulation parameters, and delivering, using the one or more stimulation electrodes, the neural stimulation to the nerve or artery/nerve plexus based on the second set of the stimulation parameters. Another illustrative embodiment of the present disclosure comprises a medical device including an implantable neurostimulator having a housing, a feedthrough assembly that passes through the housing, and an electronics module within the housing and connected to the one or more feedthroughs. The electronics module includes a pulse generator, a controller, and a memory storing program instructions. The medical device further includes a lead assembly having a lead body including a conductor material, a lead connector that connects the conductor material to the feedthrough assembly, one or more electrodes and one or more sensors connected to the conductor material. In certain embodiments, the program instructions when operated on by the controller, cause the controller to perform operations comprising: delivering neural stimulation using the pulse generator and the one or more electrodes based on a first set of stimulation parameters to a nerve or artery/nerve plexus, monitoring a response to the neural stimulation that includes monitoring responses of the nerve or artery/nerve plexus and blood-based parameters of the artery using the one or more sensors, modifying the first set of the stimulation parameters based on the blood-based parameters to create a second set of stimulation parameters, and delivering the neural stimulation using the pulse generator and the one or more electrodes based on the second set of the stimulation parameters.

Advantageously, these approaches provide neuromodulation devices and systems that are capable of detecting and/or tracking effects due to neuromodulation therapy and closing the loop on stimulation parameters. For example, the neuromodulation devices or systems described herein can adjust stimulation parameters to achieve therapeutic benefit while minimizing adverse physiological effects. Further, the neuromodulation devices or systems described herein can make the titration of neuromodulation therapy personalized to each individual patient.

II. Neuromodulation Devices or Systems

FIG. 1 shows a neuromodulation system 100 in accordance with some aspects of the present disclosure. In some embodiments, the neuromodulation system 100 includes a neurostimulator 105, one or more sensors 110, and a controller 115. The neurostimulator 105 includes software and/or electronic circuit components that record a signal from a nerve or artery/nerve plexus and generate a signal to deliver a voltage, current, optical, or ultrasonic stimulation to a nerve or artery/nerve plexus. In certain embodiments, the neurostimulator 105 is implanted within a patient at a location remote from or near to the nerve or artery/nerve plexus and is configured to record and deliver the signal to the nerve or artery/nerve plexus via one or more electrodes attached to the nerve or artery/nerve plexus. As used herein, remote means further than 6 inches, for example 8 inches from the target of stimulation such as the nerve or artery/nerve plexus, while near means within 6 inches, for example within 4 inches of the target of stimulation such as the nerve or artery/nerve plexus. In other embodiments, the neurostimulator 105 is external to the patient and configured to record and deliver the signal to the nerve or artery/nerve plexus via one or more electrodes implanted within the patient and attached to the nerve or artery/nerve plexus.

The one or more sensors 110 include software and/or electronic circuit components that sense physiological responses to the voltage, current, optical, or ultrasonic stimulation. The physiological responses may include responses of the nerve or artery/nerve plexus to the stimulation, blood-based parameter changes of the artery, or a combination thereof. In certain embodiments, the one or more sensors 110 are implanted within a patient at a location near to or attached to the nerve or artery/nerve plexus and are configured to receive signal(s) indicative of the physiological responses (e.g., nerve responses and blood-based parameter changes of the artery).

The controller 115 includes software and/or electronic circuit components that determine, sense, or record electrical activity and physiological responses via the electrodes and one or more sensors 110, control stimulation parameters of the neurostimulator 105 (e.g., control stimulation parameters based on feedback from desired or adverse physiological effects), and/or causes delivery of the stimulation via the neurostimulator 105 and electrodes. In certain embodiments, the controller 115 is implanted within a patient at a location remote from or near to the nerve or artery/nerve plexus and is in communication with the neurostimulator 105 and the one or more sensors 110 via a wired or wireless connection. In other embodiments, the controller 115 is external to the patient and is in communication with the neurostimulator 105 and the one or more sensors 110 via a wired or wireless connection.

While the neurostimulator 105, one or more sensors 110, and controller 115 are described herein as an implantable neuromodulation system with respect to several described embodiments, it should be understood that various systems and arrangements comprising the neurostimulator 105, one or more sensors 110, and controller 115 are contemplated without departing from the spirit and scope of the present disclosure. For example, the neuromodulation system 100 may include the neurostimulator 105, one or more sensors 110, and controller 115 within a distributed environment such as a cloud computing environment, and the neurostimulator 105, one or more sensors 110, and controller 115 may be in communication via one or more communication networks 120. Examples of communication networks 120 include, without restriction, the Internet, a wide area network (WAN), a local area network (LAN), an Ethernet network, a public or private network, a wired network, a wireless network, and the like, and combinations thereof.

Figure 2:
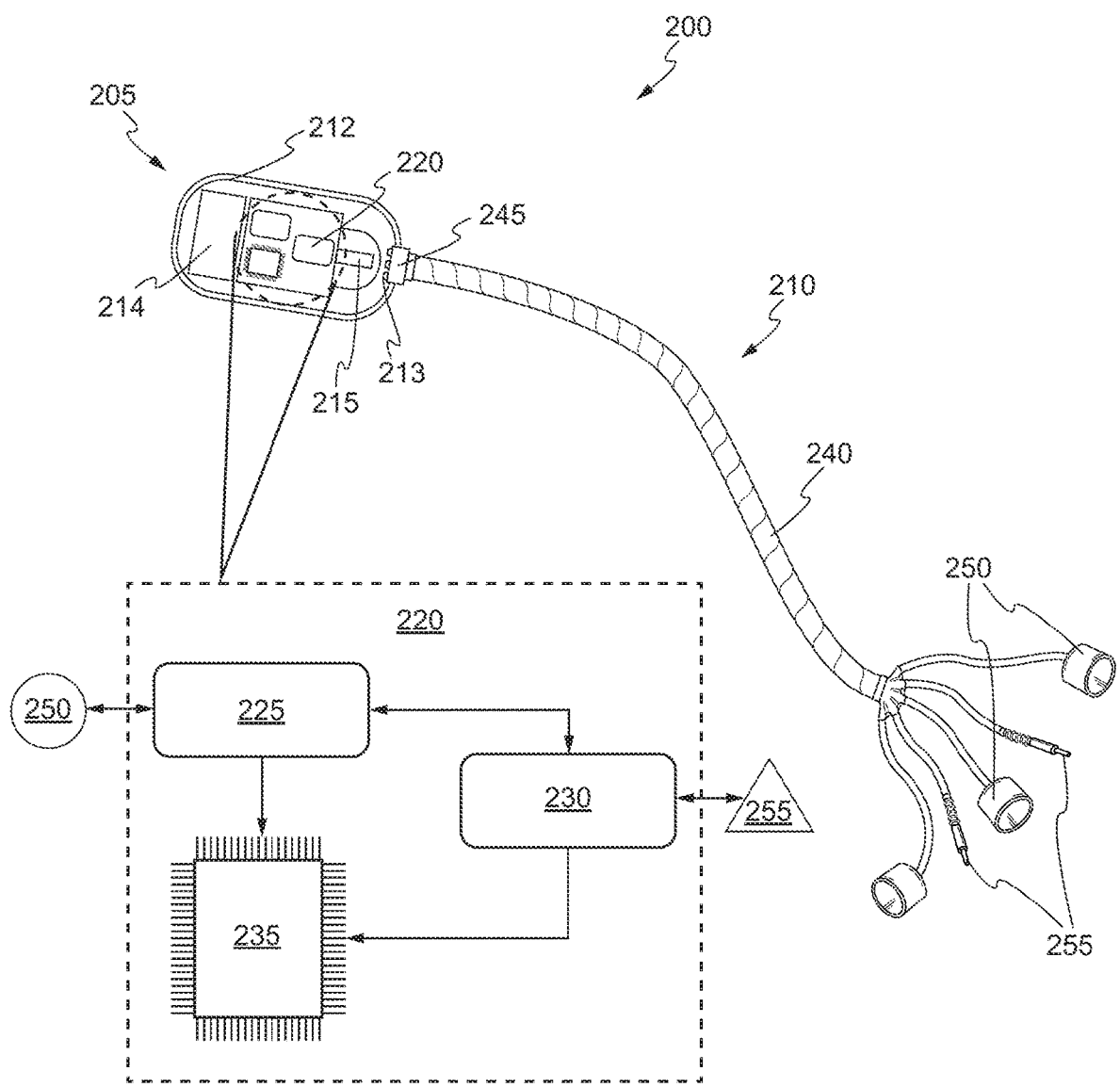
FIG. 2 shows an shows an implantable neuromodulation system in accordance with some aspects of the present disclosure.

FIG. 2 shows a neuromodulation system 200 in accordance with some aspects of the present disclosure. In various embodiments, the neuromodulation system 200 includes an implantable neurostimulator 205 (e.g., a neurostimulator 105 as described with respect to FIG. 1) and a lead assembly 210. The implantable neurostimulator 205 may include a housing 212, a feedthrough assembly 213, a power source 214, an antenna 215, and an electronics module 220 (e.g., a computing system). The housing 105 may be comprised of materials that are biocompatible such as bioceramics or bioglasses for radio frequency transparency, or metals such as titanium. In accordance with some aspects of the present disclosure, the size and shape of the housing 212 are selected such that the neurostimulator 205 can be implanted within a patient. The feedthrough assembly 213 is attached to a hole in a surface of the housing 212 such that the housing 212 is hermetically sealed. The feedthrough assembly 213 may include one or more feedthroughs (i.e., electrically conductive elements, pins, wires, tabs, pads, etc.) mounted within and extending through the surface of the housing 212 or a cap from an interior to an exterior of the housing 212. The power source 214 may be within the housing 212 and connected (e.g., electrically connected) to the electronics module 220 to power and operate the components of the electronics module 220. The antenna 215 may be connected (e.g., electrically connected) to the electronics module 220 for wireless communication with external devices via, for example, radiofrequency (RF) telemetry.

In some embodiments, the electronics module 220 is connected (e.g., electrically connected) to interior ends of the feedthrough assembly 213 such that the electronics module 220 is able to apply a signal or electrical current to leads of the lead assembly 210 connected to exterior ends of the feedthrough assembly 213. The electronics module 220 includes discrete and/or integrated electronic circuit components that implement analog and/or digital circuits capable of producing the functions attributed to the neuromodulation devices or systems described herein. In various embodiments, the electronics module 215 includes software and/or electronic circuit components such as a pulse generator 225 that generates a signal to deliver a voltage, current, optical, or ultrasonic stimulation to a nerve or artery/nerve plexus via electrodes, a controller 230 (e.g., a controller 115 as described with respect to FIG. 1) that determines, senses, or records electrical activity and physiological responses via the electrodes and sensors, controls stimulation parameters of the pulse generator 225 (e.g., control stimulation parameters based on feedback from the physiological responses), and/or causes delivery of the stimulation via the pulse generator 225 and electrodes, and a memory 235 with program instructions operable on by the pulse generator 225 and the controller 230 to perform one or more processes described herein.

In certain embodiments, the electronics module 220 is a printed circuit board with an interposer in combination with discrete and/or integrated electronic circuit components such as application specific integrated circuits (ASICs). The electronics module 220 can be remotely accessed following implant through an external programmer, such as an external computing device. For example, the external programmer can be used by healthcare professionals to check and program the electronics module 220 after implantation in a patient and to adjust stimulation parameters during a stimulation process, e.g., providing an initial set of the stimulation parameters. The external programmer may communicate with the electronics module 220 via wired or wireless communication methods, such as, e.g., wireless radio frequency transmission.

The pulse generator 225 is configured to set or adjust one or more stimulation parameters based on commands from the controller 230. Examples of stimulation parameters include burst duration, burst interval, stimulation amplitude (e.g., stimulation strength), pulse width, frequency, duty cycle, stimulation waveform shape, and electrode configuration. In some embodiments, neural stimulation is delivered via the pulse generator 225 in a stimulation burst, which is a train of stimulation pulses programmed with any combination of stimulation amplitude, pulse width, stimulation waveform shape, and signal frequency. Stimulation bursts can be characterized by burst durations and burst intervals. Burst duration is the length of time that a burst lasts. Burst interval can be identified by the time between the start of successive bursts. The pattern of bursts can include any combination of burst durations and burst intervals. A simple burst pattern with one burst duration and burst interval can continue periodically for a programmed period or can follow a more complicated schedule. The programmed pattern of bursts can be composed of multiple burst durations and burst interval sequences. The programmed pattern of bursts can be characterized by a duty cycle, which refers to a repeating cycle of neural stimulation ON for a fixed time and neural stimulation OFF for a fixed time.

In other embodiments, the pulse generator 225 is adapted to change electrode configuration as part of the neural stimulation in combination with or separate from changes to the other stimulation parameters such as burst duration, burst interval, stimulation amplitude, pulse width, frequency, stimulation waveform shape, and duty cycle. For example, the implantable neurostimulator 205 may include electrode configuration switches, and the switches may be configured to deliver neural stimulation from the pulse generator 225 to selected one or more electrodes. In some embodiments, the pulse generator 225 is configured to control the switches to generate a signal or electrical current to deliver neural stimulation to a nerve or artery/nerve plexus based on one or more stimulation parameters via a desired electrode configuration. In other embodiments, the controller 230 is configured to control the switches and cause the pulse generator 225 to generate a signal or electrical current to deliver neural stimulation to a nerve or artery/nerve plexus based on one or more stimulation parameters via a desired electrode configuration The controller 230 is capable of being implemented using hardware, software, firmware or combinations thereof. In various embodiments, the controller 230 includes one or more processors to perform instructions embedded in the memory 235 to perform functions associated with the neural stimulation therapy, such as performing neural stimulation based on a stimulation or titration schedule stored in the memory 235 and/or based on feedback received via the electrodes and sensors. The controller 230 is in communication with the pulse generator 225 and the one or more sensors. For example, the controller 230 may be configured to perform functions associated with the neural stimulation therapy including (i) delivering, using a pulse generator 225 and at least one stimulation electrode, neural stimulation based on a first set of the stimulation parameters, (ii) monitoring a response to the neural stimulation that includes (a) monitoring, using one or more sensors such as a recording electrode, electrographic activity of the nerve or artery/nerve plexus and (b) monitoring, using one or more sensors such as a blood pressure sensor blood-based parameter changes of an artery, or a combination thereof, (iii) modifying, using a processor, the first set of the stimulation parameters based on the monitoring to create a second set of stimulation parameters, and (iv) delivering, using the pulse generator 225 and at least one stimulation electrode, the neural stimulation based on the second set of the stimulation parameters.

The memory 235 may be a non-transitory machine readable storage medium having instructions stored thereon that when executed by a processor (e.g., a processor of the controller 230) causes the processor to perform one or more operations such as generation of a signal or electric current based on one or more stimulation parameters. In some embodiments, the memory 235 includes instructions operable on by the controller 230 to cause the on-demand stimulation therapy, receive therapy feedback and modify the therapy based on the feedback. The modification may include gradually increasing or decreasing the intensity of the neural stimulation signal to a desired or target therapeutic level while taking into consideration blood-based parameter changes of an artery. In other embodiments, the memory 235 includes instructions operable on by the controller 230 to control titration of the therapy. During the titration, the neural stimulation signal may be delivered using different combinations of stimulation parameters and the effects of the stimulation (e.g., the desired physiological effects and/or adverse physiological effects such as increased/decreased blood pressure) are evaluated for the different parameter combinations to determine an optimal set or combination of stimulation parameters that provide the desired therapeutic effect while minimizing or preventing adverse physiological effects. In yet other embodiments, the memory includes instructions operable on by the controller to adjust or select a combination of stimulation parameters that is determined to be effective at generating a desired physiological effect while using feedback from blood-based parameter changes to minimize or prevent adverse physiological effects such as restricted blood flow.

The lead assembly 210 may include a lead body 240, a lead connector 245, one or more electrodes 250, and one or more sensors 255. In some embodiments, the lead connector 245 is bonding material that bonds conductor material of the lead body 240 to the electronics module 220 of the implantable neurostimulator 205 via the feedthrough assembly 213. The bonding material may be a conductive epoxy or a metallic solder or weld such as platinum. In other embodiments, the lead connector 245 is conductive wire or tab (e.g., a wire or tab formed of copper, silver, or gold) that bonds conductor material of the lead body 240 to the electronics module 220 of the implantable neurostimulator 205. In alternative embodiments, the implantable neurostimulator 205 and the lead body 240 may be designed to connect with one another via a lead connector 245 such as a pin and sleeve connector, snap and lock connector, flexible printed circuit connectors, or other means known to those of ordinary skill in the art.

The lead body 240 may include one or more leads of conductive material and insulator. The one or more leads carry electrical conductors that allow electrical coupling of the electronics module 220 to the one or more electrodes 250 via the lead connector 245. In some examples the one or more leads are extruded with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, the conductive material for the one or more leads may serve as a strengthening member onto which the body of the lead is extruded. For example, a distal electrode may couple to a centrally located wire on which the body of lead is extruded. The conductive material may be any suitable conductor such as stainless steel, silver, copper or other conductive materials, which may have separate coatings or sheathing for anticorrosive, insulative and/or protective reasons. The conductive material may take various forms including wires, drawn filled tubes, helical coiled conductors, microwires, and/or printed circuits, for example.

The one or more electrodes 250 may be connected to the conductor material of the lead body 240 via the one or more leads. In some embodiments, the one or more electrodes 250 are placed around, within or adjacent to a nerve or artery/nerve plexus to: (i) stimulate the nerve or artery/nerve plexus and/or (ii) sense electrical impulses traveling through the nerve or artery/nerve plexus. For example, a peripheral nerve cuff placed around a nerve or artery/nerve plexus may comprise an array of recording and stimulation electrodes 250. The one or more electrodes 250 may be formed of a conductive material such as a copper, silver, gold, platinum, stainless steel, nickel-cobalt base alloy, platinum-iridium alloy, brass, bronze, aluminum, etc., and take the form of book electrodes, cuff electrodes, spiral cuff electrodes, epidural electrodes, helical electrodes, probe electrodes, linear electrodes, paddle electrodes, and intraneural electrodes, for example.

The one or more sensors 255 may be connected to the conductor material of the lead body 240 via the one or more leads. In some embodiments, the one or more sensors 255 are placed around, within or adjacent to a nerve or artery/nerve plexus to sense physiological response of the nerve or artery/nerve plexus to the voltage, current, optical, or ultrasonic stimulation. The physiological responses may include nerve responses (e.g., desired or targeted physiological effects), blood-based parameter changes (e.g., blood pressure changes), or a combination thereof. In various embodiments the one or more sensors 255 used to sense nerve responses such as electrical impulses traveling through the nerve or artery/nerve plexus include one or more recording electrodes. In various embodiments the one or more sensors 255 used to sense the blood-based parameter changes include one or more of: (i) a blood flow sensor such as a Doppler sensor or impedance sensor, (ii) a blood pressure sensor such as a piezoresistive pressure sensor or impedance sensor, and (iii) a distension sensor such as a capacitive sensor, a Doppler sensor, or a photonic sensor.

The arterial system has two interrelated hemodynamic functions: (i) a conduit function to deliver an adequate blood supply from the heart to peripheral tissues, and (ii) a cushioning or dampening function to dampen blood flow and pressure oscillations caused by the intermittent character of the left ventricle ejection ensuring peripheral organ perfusion at steady flow and pressure. Neural stimulation to a nerve or artery/nerve plexus such as the peripheral nerves at the splenic artery or the splenic artery/nerve plexus (close to the end-organ) to innervate the spleen may control inflammation; however, the neural stimulation may also adversely affect the conduit and/or cushioning/dampening function of the artery. In order to ensure that the neural stimulation is delivered in a manner that that achieves the desired physiological effect while minimizing or preventing adverse physiological effects to the artery, various embodiments discussed herein monitor one or more blood-based parameter parameters, for example, blood flow, blood pressure, and arterial distension, of the artery to optimize neuromodulation stimulation parameters based on feedback from stimulus evoked blood parameter changes.

In some embodiments, a blood flow sensor such as a Doppler sensor is configured to measure blood velocity by detecting a difference in frequency between an emitted burst of ultrasound and returning echoes from moving blood. For example, in a pulsed-Doppler system the sample volume can be adjusted in depth by varying the time delay between transmission of a short ultrasonic burst and sampling of the returning echoes. The resulting Doppler signal, which is usually in the audible range, is a summation of the Doppler-shifted echoes from many blood cells moving at different velocities, and the spectrum of frequencies represents the distribution of red cell velocities within the sample volume. The red cell velocities can be correlated to a measurement of overall velocity of blood flow within the artery.

In other embodiments, a blood flow sensor such as an impedance sensor is configured to detect changes in the electrical impedance of blood. For example, there is a strong correlation between electrical impedance and viscosity of blood. If a person has inflammation (such as with rheumatoid arthritis), then there is an increased risk that the red blood cells will aggregate. This aggregation increases the risk for heart attack or strokes. Another important factor for aggregation beyond inflammation is the viscosity of blood. In particular, plasma resistance and cell membrane capacitance, which are both factors for electrical impedance, are affected by blood viscosity. The changes in the one or more parameters including plasma resistance, cell membrane capacitance, and overall electrical impedance may be measured as the viscosity of the blood and correlated to overall velocity of blood flow within the artery.

In some embodiments, a pressure sensor such as an impedance sensor is configured to measure blood pressure. For example, blood pressure within an artery can be determined based on the measurement of a pulse wave velocity. The pulse wave velocity is the velocity at which pressure pulses propagate along the arterial wall. The pulse wave velocity may be measured and correlated to changes in the blood pressure.

In other embodiments, a pressure sensor such as piezoresistive pressure sensor is configured to measure blood pressure. For example, a pressure sensor may include a diaphragm formed on a substrate (e.g., silicon), which bends with applied pressure. A deformation occurs in the crystal lattice of the diaphragm because of the bending. This deformation causes a change in the band structure of piezoresistors that may be placed on the diaphragm, leading to a change (i.e., increase or decrease according to orientation of the piezoresistors) in the resistivity of the material. The change in resistivity may be measured and correlated to blood pressure.

In some embodiments, a distension sensor such as a capacitive sensor is configured to measure arterial distension. For example, a distension sensor may include an oscillator and a capacitor. As the capacitor changes its capacitance in accordance with the change in blood pressure within the artery, the frequency of the oscillator changes as well. The change in resonant frequency (inclusive of the associative inductance or capacitance in low frequency, or self-resonant in high frequency) is a function of the change in distension to pressure applied to the artery, and may be measured and correlated to arterial distension.

In other embodiments, the distension sensor such as a photonic sensor is configured to measure arterial distension. For example, the distension sensor may include stretchable optoelectronic sensors applied to the artery that are capable of detecting distension of the arterial wall based on transmission photoplethysmography. Photoplethysmography is performed by detecting a change in amount of photons transmitted across a distending artery over a cardiac cycle. The change in amount of photons transmitted may be measured and correlated to arterial distension.

In yet other embodiments, a distension sensor such as a Doppler sensor is configured to measure cardiac motion and artery diameter pulsation, which when combined with blood pressure may provide an index of vessel compliance. For example, the Doppler sensor may be configured to measure the phase of blood echoes that advance (or recede) continuously to generate the Doppler shift frequency. Echoes from slower moving solid structures such as blood vessel walls that move back and forth generate phase signals which advance and recede with each cardiac cycle. Under optimal conditions, the Doppler sensor can resolve about 1° of phase or 0.1 μm of tissue motion and can determine arterial distension continuously throughout a cardiac cycle.

While the one or more sensors 255 has been described at some length and with some particularity with respect to several described embodiments, it is not intended that the sensors be limited to any such particular technology or particular embodiment. Instead, it should be understood that the described embodiments are provided as examples of sensors, and the one or more sensors 255 are to be construed with the broadest sense to include variations of sensors listed above, as well as other variations that are well known to those of ordinary skill in the art.

III. Methods for Delivering Neuromodulation

Figure 3:
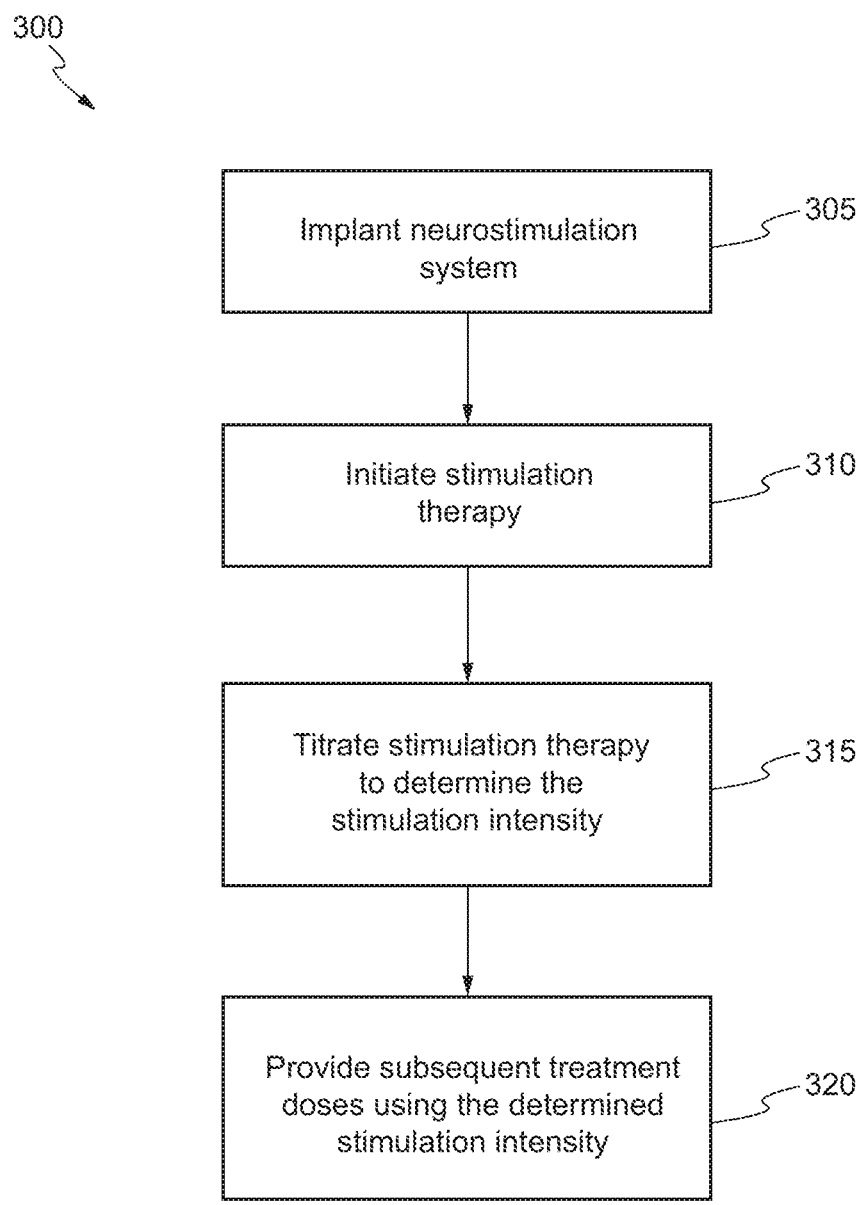
FIGS. 3-5 show exemplary flows for titrating neuromodulation therapy and providing neuromodulation therapy in accordance with some aspects of the present disclosure.
Figure 4:
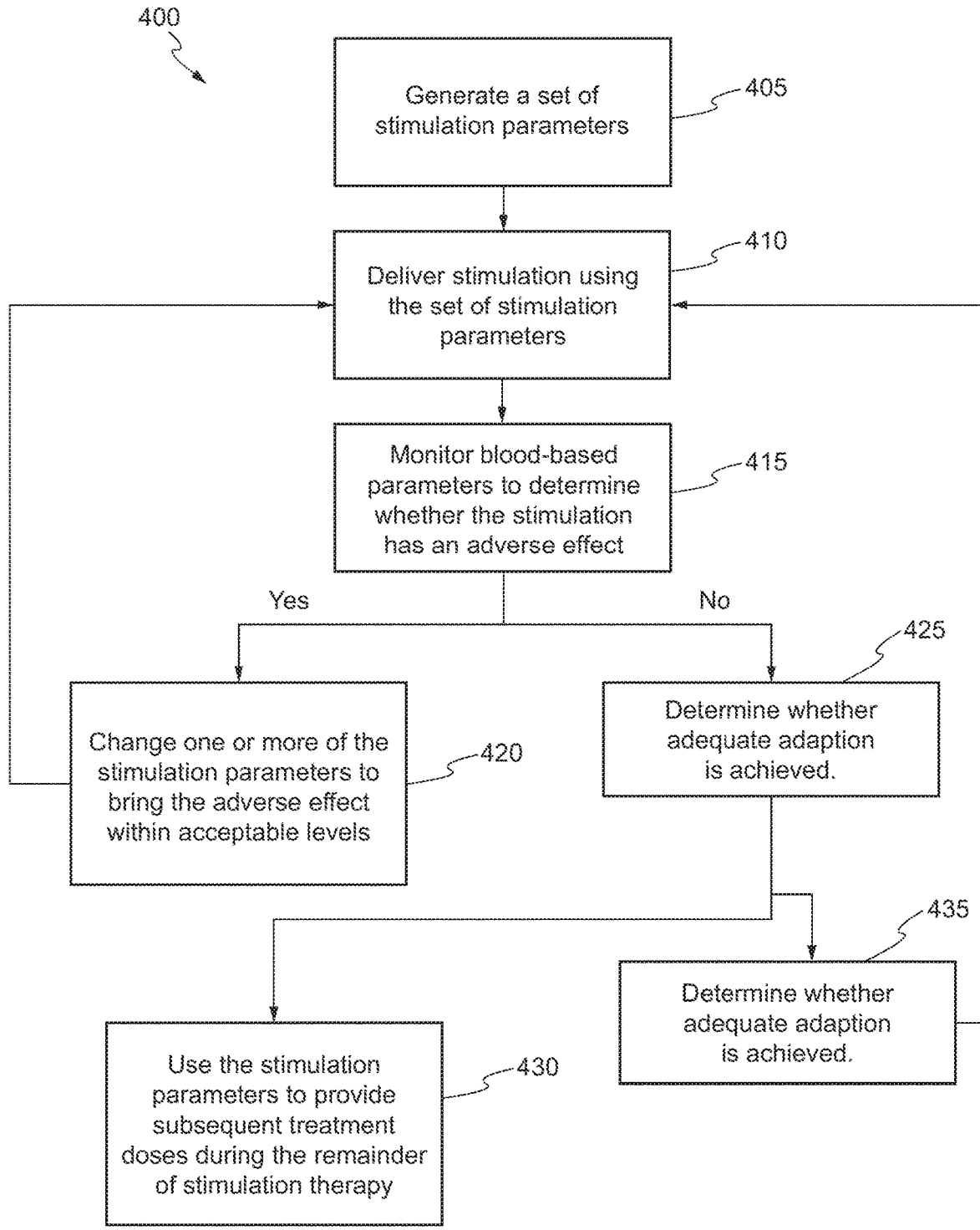
Figure 5:
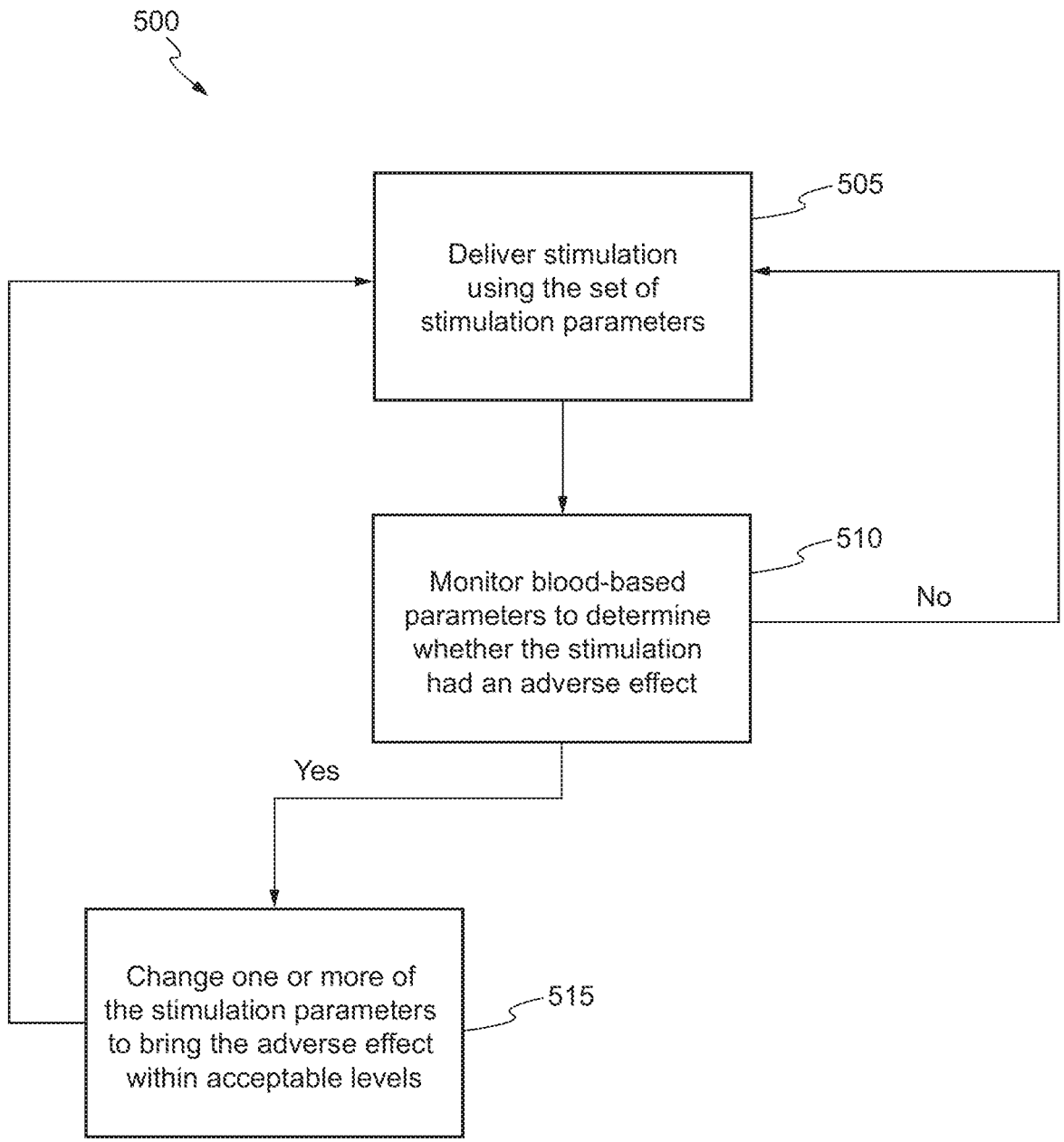

FIGS. 3-5 depict simplified flowcharts depicting processing performed for delivering neuromodulation according to embodiments of the present disclosure. As noted herein, the flowcharts of FIGS. 3-5 illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 3 depicts a simplified flowchart 300 illustrating a titration process used to gradually increase stimulation intensity (i.e., a combination of one or more of the stimulation parameters) to a desired therapeutic level. As will be described in greater detail below, a desired therapeutic level may be defined based on a composite target intensity level comprising one or more of the following: a target level for one or more of the stimulation parameters and a target physiological effect. If the stimulation intensity is increased too quickly or beyond a certain threshold, which can be patient dependent, the patient may experience adverse physiological effects, such as an increase/decrease in blood pressure or blood flow. The titration process gradually increases stimulation intensity within a tolerable level, and maintains that intensity for a period of time to permit the patient to adjust to each increase in intensity, thereby gradually increasing the stimulation intensity towards a desired physiological effect while monitoring for adverse physiological effects. The titration process continues until adequate adaptation is achieved. In various embodiments, adequate adaptation includes achieving one or more of the following objectives: acceptable levels for the blood-based parameter parameters, a target intensity level, and a target physiological effect. As will be described in greater detail below, adequate adaptation may be determined based on a composite threshold comprising one or more of the following: an acceptable level for one or more blood-based parameters, a target intensity level for one or more stimulation parameters, and a target physiological effect. In some embodiments, the titration process is automated and is executed by the implanted device without manual adjustment of the stimulation intensity by the patient or health care provider.

In 305, a neuromodulation system (e.g., neuromodulation system 100 described with respect to FIG. 1), including an implantable neurostimulator and a lead assembly is implanted in a patient. In some embodiments, electrodes of the lead assembly are connected to a nerve or artery/nerve plexus such as the peripheral nerves near the splenic artery or the splenic artery/nerve plexus. In 310, a stimulation therapy process is initiated. In some embodiments, the stimulation therapy is initiated after an optional post-surgery recovery period (e.g., a number of days/weeks), during which time no stimulation therapy occurs. In alternative embodiments, the stimulation therapy is initiated shortly (e.g., hours) or immediately after implantation. Initiation of the stimulation therapy may include obtaining or generating an initial set of stimulation parameters and providing stimulation to the patient using the initial set of stimulation parameters. The initial set of stimulation parameters may comprise one or more of an initial burst duration, initial burst interval, initial stimulation amplitude, initial pulse width, initial frequency, initial duty cycle, initial stimulation waveform shape, and initial electrode configuration. The various initial parameter settings may vary, but may be selected so that one or more of the parameters are set at levels below a predefined target parameter set level, such that the titration process is used to gradually increase the intensity parameters to achieve adequate adaptation. In some embodiments, the initial burst duration, the initial burst interval, the initial frequency, and initial electrode configuration are set at target levels or configurations, while the initial stimulation amplitude, initial pulse width, stimulation waveform shape, and initial duty cycle are set below their respective target levels. In other embodiments, the initial electrode configuration is set at a target level or configuration, while the initial burst duration, the initial burst interval, the initial frequency, the initial stimulation amplitude, the initial pulse width, stimulation waveform shape, and the initial duty cycle are set below their respective target levels.

In 315, stimulation therapy is provided using the initial set of stimulation parameters and titrated by setting or adjusting the stimulation parameters using a titration schedule to obtain or generate subsequent sets of stimulation parameters with the goal of achieving adequate adaptation. In some embodiments, the titration process includes delivering stimulation using a neurostimulator based on a set of stimulation parameters, monitoring a response to the stimulation that includes monitoring of nerve responses, blood-based parameter changes, or a combination thereof, modifying one or more of the stimulation parameters based on a titration schedule, the nerve responses, and/or the blood-based parameter changes to create a subsequent set of stimulation parameters, and delivering the neural stimulation using the neurostimulator based on the subsequent set of stimulation parameters. This process may be repeated until adequate adaptation is achieved. In some embodiments, adequate adaptation includes achieving one or more of the following objectives: acceptable levels for the blood-based parameters, a target intensity level for one or more stimulation parameters, and a target physiological effect. The achievement of one or more of these objectives determines the stimulation intensity including a therapeutic set of stimulation parameters to be used for subsequent treatment doses delivered during the remainder of stimulation therapy in 320, as further described herein with respect to FIG. 5.

FIG. 4 depicts a simplified flowchart 400 illustrating a detailed titration process used to gradually increase stimulation intensity to a desired therapeutic level. In some embodiments, titration sessions are automatically initiated by the neuromodulation system or initiated by the patient without requiring any intervention by the health care provider. This can eliminate the need for the patient to schedule a subsequent visit to the health care provider, thereby potentially reducing the total amount of time needed for the titration process to complete. In these embodiments, the neuromodulation system may include the one or more sensors, e.g., a blood flow sensor, a blood pressure sensor, and a distension sensor, that communicates with the neuromodulation system's control system to enable the control system to detect the patient's physiological response to the titration and automatically make adjustments to the titration processes described herein with reduced or no inputs from the patient or health care provider. The monitored signals can also enable the control system to detect when the target physiological effect has been achieved and conclude the titration process. The neuromodulation system could in addition or alternatively include a patient control input to permit the patient to communicate to the control system that an acceptable adverse physiological effect level has been exceeded. In these automatically initiated titration sessions, the neuromodulation system may be configured to wait a period of time after completing one session before initiating the next session. This period of time may be predetermined, e.g., two or three days, or programmable.

At 405, the neuromodulation system is configured to obtain or generate a set of stimulation parameters. For example, in some embodiments, when initiating an initial titration session (e.g., 310 as described with respect to FIG. 3), the neuromodulation system is configured to obtain or generate an initial set of stimulation parameters to initialize the stimulation therapy. In other embodiments, when executing a subsequent titration session (e.g., a maintenance titration session), the neurostimulator is configured to obtain or generate a set of stimulation parameters based on the previously determined therapeutic set of stimulation parameters (e.g., 320 as described with respect to FIG. 3).

In 410, the neuromodulation system delivers stimulation to the patient using the set of stimulation parameters (e.g., a first set of stimulation parameters). If this is the first titration session, then the stimulation would be delivered with the initial set of stimulation parameters described above with respect to 310. If this is a subsequent titration session, then the stimulation intensity would remain at the same level at the conclusion of the previous titration session described above with respect to 320 of FIG. 3. In some embodiments, the stimulation is a stimulation signal or electrical current.

In 415, the neuromodulation system monitors nerve responses (e.g., electrical impulses traveling through the nerve or artery/nerve plexus) and blood-based parameters (e.g., blood flow, blood pressure, and arterial distension) using one or more sensors (e.g., sensors 255 described with respect to FIG. 2) to determine whether the stimulation provided using the set of stimulation parameters had zero or minimal physiological effect, achieved a target physiological effect, and/or had an adverse physiological effect on the patient. In various embodiments, the monitoring includes the neuromodulation system obtaining the blood-based parameters and comparing the blood-based parameters to one or more predetermined thresholds to determine whether the stimulation had an adverse physiological effect. When the stimulation provided using a set of stimulation parameters is determined to have had an adverse physiological effect, the process proceeds to 420. When the stimulation provided using a set of stimulation parameters is determined to not have had an adverse physiological effect, the process proceeds to 425. In determining whether the stimulation had an adverse physiological effect, the neuromodulation system may be configured to wait a period of time after delivering the stimulation in [410 before determining whether the stimulation did not have an adverse physiological effect and proceeding to 425. This period of time may be predetermined, e.g., two or three days, or programmable at which time the neuromodulation system continues to monitor the blood-based parameters for an adverse physiological effect.

In some embodiments, prior to neural stimulation, baseline values for blood flow, blood pressure, and arterial distension may be determined and recorded for a patient. Once neural stimulation begins on the patient, the values obtained for blood flow, blood pressure, and arterial distension may be compared respectively to the baseline values for blood flow, blood pressure, and arterial distension to determine the extent of change in the blood-based parameters. The determined extent of change for each blood-based parameter may then be compared to predetermined threshold values set for each blood-based parameter (e.g., threshold values that may be indicative of an adverse physiological effect) to determine whether the stimulation provided using a set of stimulation parameters had an adverse physiological effect on the blood flow, the blood pressure, or the arterial distension. As will be described in greater detail below, an adverse physiological effect may be determined based on the change for each blood-based parameter or based on a combination of the changes for the blood-based parameters.

In alternative embodiments, the monitoring includes the neuromodulation system obtaining the blood-based parameters and comparing each of the blood-based parameters to a predetermined threshold for each of the blood-based parameters to determine whether the stimulation had an adverse physiological effect. For example, once neural stimulation begins on the patient, the values obtained for blood flow, blood pressure, and arterial distension may be compared respectively to predetermined threshold values set for each blood-based parameter (e.g., threshold values that may be indicative of an adverse physiological effect) to determine whether the stimulation provided using a set of stimulation parameters had an adverse physiological effect on the blood flow, the blood pressure, or the arterial distension. As will be described in greater detail below, an adverse physiological effect may be determined based on each blood-based parameter or based on a combination of the blood-based parameters.

In 420, one or more of the stimulation parameters is modified to bring the adverse physiological effect within acceptable levels. In various embodiments, one or more of the stimulation parameters is modified (e.g., using the one or more processors) based on the responses of the nerve or artery/nerve plexus and/or the blood-based parameters to create a modified set of stimulation parameters (e.g., a second set of stimulation parameters). In some embodiments, one or more of the burst duration, the burst interval, the stimulation amplitude, the pulse width, the frequency, the duty cycle, stimulation waveform shape, and the electrode configuration is changed to bring the adverse physiological effect within acceptable levels. The changes in the parameter settings may vary, but may be selected so that one or more of the parameters are set at levels below previously set levels, such that the adverse physiological effect is minimized or prevented. In some embodiments, the burst duration, the burst interval, the frequency, and electrode configuration are maintained at target levels or configurations, while one or more of the stimulation amplitude, the pulse width, stimulation waveform shape, and the duty cycle are reduced below their respective previous levels. In other embodiments, the initial electrode configuration is set at a target level or configuration, while one or more of the burst duration, the burst interval, the frequency, the stimulation amplitude, the pulse width, stimulation waveform shape, and the duty cycle are reduced below their respective previous levels. Once the one or more of the stimulation parameters are modified, the process proceeds to 410, to deliver stimulation to the patient using the modified set of stimulation parameters and monitor nerve responses and the blood-based parameters to determine whether the stimulation provided using the modified set of stimulation parameters achieved a target physiological effect and/or still had an adverse physiological effect on the patient.

In 425, a determination is made as to whether adequate adaptation is achieved. In some embodiments, adequate adaptation includes achieving one or more of the following objectives: acceptable levels for the blood-based parameters, a target intensity level for one or more stimulation parameters, and a target physiological effect. When the stimulation provided using a set of stimulation parameters is determined to achieve adequate adaptation, the process proceeds to 430. When the stimulation provided using a set of stimulation parameters is determined to not achieve adequate adaptation, the process proceeds to 435.

At 430, the neuromodulation system delivers stimulation to the patient using the set of stimulation parameters during the remainder of stimulation therapy, as further described herein with respect to FIG. 5.

At 435, one or more of the stimulation parameters is modified to achieve one or more of the following objectives: acceptable levels for the blood-based parameters, a target intensity level for one or more stimulation parameters, and a target physiological effect. In various embodiments, one or more of the stimulation parameters is modified based on the responses of the nerve or artery/nerve plexus and/or the blood-based parameters to create a modified set of stimulation parameters. In some embodiments, one or more of the burst duration, the burst interval, the stimulation amplitude, the pulse width, the frequency, the duty cycle, stimulation waveform shape, and the electrode configuration is changed to achieve one or more of the following objectives: acceptable levels for the blood-based parameters, a target intensity level for one or more stimulation parameters, and a target physiological effect. The changes in the parameter settings may vary, but may be selected so that one or more of the parameters are set at levels above or below previously set levels, such that acceptable levels for the blood-based parameters are obtained, a target intensity level for one or more stimulation parameters is obtained, and a target physiological effect is obtained. In some embodiments, the burst duration, the burst interval, the frequency, and electrode configuration are maintained at target levels or configurations, while one or more of the stimulation amplitude, the pulse width, stimulation waveform shape, and the duty cycle are increased above their respective previous levels towards target levels. In other embodiments, the initial electrode configuration is set at a target level or configuration, while one or more of the burst duration, the burst interval, the frequency, the stimulation amplitude, the pulse width, stimulation waveform shape, and the duty cycle are increased above their respective previous levels towards target levels. Once the one or more of the stimulation parameters are modified, the process proceeds to step 410, to deliver stimulation to the patient using the modified set of stimulation parameters and monitor nerve responses and the blood-based parameters to determine whether the stimulation provided using the modified set of stimulation parameters now achieves adequate adaptation.

FIG. 5 depicts a simplified flowchart 500 illustrating a process used to provide a therapeutic level of neural stimulation to achieve a desired or target physiological effect during a remainder of stimulation therapy while minimizing or preventing an adverse physiological effect. In some embodiments, the remainder of stimulation therapy is automatically performed by the neuromodulation system without requiring any intervention by the patient or health care provider. This can eliminate the need for the patient to schedule a subsequent visit to the health care provider, thereby potentially reducing prolong adverse physiological effects suffered by a patient. In these embodiments, the neuromodulation system may include the one or more sensors, e.g., a blood flow sensor, a blood pressure sensor, and a distension sensor, that communicates with the neuromodulation system's control system to enable the control system to detect the patient's physiological responses to the stimulation therapy and automatically make adjustments to the stimulation therapy processes described herein with reduced or no inputs from the patient or health care provider. The monitored signals can also enable the control system to detect when the target physiological effect has been achieved and maintain the stimulation therapy process. The neuromodulation system could in addition or alternatively include a patient control input to permit the patient to communicate to the control system that an acceptable adverse physiological effect level has been exceeded. In automatically controlled stimulation therapy processes, the neuromodulation system may be configured to wait a period of time after completing one process, e.g., delivering stimulation, before initiating the changing one or more of the stimulation parameters. This period of time may be predetermined, e.g., two or three days, or programmable.

In 505, the neuromodulation system delivers stimulation to the patient using a set of stimulation parameters. In some embodiments, the set of stimulation parameters are the set of stimulation parameters determined in 315 or 425 of FIGS. 3 and 4, respectively, that has achieved adequate adaptation. In 510, the neuromodulation system monitors nerve responses (e.g., electrical impulses traveling through the nerve or artery/nerve plexus) and blood-based parameters (e.g., blood flow, blood pressure, and arterial distension) using one or more sensors (e.g., sensors 255 described with respect to FIG. 2) to determine whether the stimulation provided using the set of stimulation parameters had zero or minimal physiological effect, achieved a desired physiological effect, and/or had an adverse physiological effect on the patient (e.g., occlusion of an artery). In various embodiments, the monitoring includes the neuromodulation system obtaining the blood-based parameters and comparing the blood-based parameters to one or more predetermined thresholds to determine whether the stimulation had an adverse physiological effect on the blood-based parameters. When the stimulation provided using a set of stimulation parameters is determined to have had an adverse physiological effect on the blood-based parameters, the process proceeds to 515. When the stimulation provided using a set of stimulation parameters is determined to not have had an adverse physiological effect on the blood-based parameters, the process continues to monitor nerve responses and the blood-based parameters through-out the remainder of the stimulation therapy.

In some embodiments, prior to neural stimulation, baseline values for blood flow, blood pressure, and arterial distension may be determined and recorded for a patient. In some embodiments, the baseline values may be recorded in the memory of the neuromodulation system (e.g., the memory 235 as described with respect to FIG. 2). Once neural stimulation begins on the patient, the values obtained for blood flow, blood pressure, and arterial distension may be compared respectively to the baseline values for blood flow, blood pressure, and arterial distension to determine the extent of change in the blood-based parameters. The determined extent of change for each blood-based parameter may then be compared to predetermined threshold values set for each blood-based parameter (e.g., threshold values that are indicative of an adverse physiological effect) to determine whether the stimulation provided using a set of stimulation parameters had an adverse physiological effect on the blood flow, the blood pressure, or the arterial distension.

An adverse physiological effect may be determined based on the change for each blood-based parameter. For example, in some embodiments, if one, two, three or more of the changes for each blood-based parameter exceeds one or more of the predetermined threshold values, then an adverse physiological effect is determined. In other embodiments, the blood-based parameters may be assigned weights or priority, for example blood flow may be designated a priority status. If (i) one, two, three or more of the weighted changes for each blood-based parameter exceed one or more of the predetermined threshold values, or (ii) the changes for one or more blood-based parameters that has priority status exceeds one or more of the predetermined threshold values, then an adverse physiological effect is determined. The predetermined threshold values may vary, e.g., from patient to patient, but may be selected such that the stimulation therapy process is configured to provide a closed-loop adjustment of the stimulation parameters based on blood parameter sensing to minimize or prevent the adverse physiological effect from reoccurring during the remainder of stimulation therapy.

Optionally, the adverse physiological effect may be determined based on a combination of the changes for the blood-based parameters. For example, in some embodiments, a composite predetermined threshold may be set that takes into consideration a combination of the changes in blood-based parameters. If the combination in the changes of the blood-based parameters exceeds the composite predetermined threshold, then an adverse physiological effect is determined. In other embodiments, the blood-based parameters may be assigned weights, for example blood flow may be designated a greater weight than blood pressure. If the combination in the weighted changes of the blood-based parameters exceeds the composite predetermined threshold, then an adverse physiological effect is determined. The composite predetermined threshold may vary, e.g., from patient to patient, but may be selected such that the stimulation therapy process is configured to provide a closed-loop adjustment of the stimulation parameters based on blood parameter sensing to minimize or prevent the adverse physiological effect from reoccurring during the remainder of stimulation therapy.

In alternative embodiments, the monitoring includes the neuromodulation system obtaining the blood-based parameters and comparing each of the blood-based parameters to a predetermined threshold for each of the blood-based parameters to determine whether the stimulation had an adverse physiological effect on the blood-based parameters. For example, once neural stimulation begins on the patient, the values obtained for blood flow, blood pressure, and arterial distension may be compared respectively to predetermined threshold values set for each blood-based parameter (e.g., threshold values that are indicative of an adverse physiological effect) to determine whether the stimulation provided using a set of stimulation parameters had an adverse physiological effect on the blood flow, the blood pressure, or the arterial distension.

An adverse physiological effect may be determined based on each blood-based parameter. For example, in some embodiments, if one, two, three or more of the blood-based parameters exceed one or more of the predetermined threshold values, then an adverse physiological effect is determined. In other embodiments, the blood-based parameters may be assigned weights or priority, for example blood flow may be designated a priority status. If (i) one, two, three or more of the weighted blood-based parameters exceed one or more of the predetermined threshold values, or (ii) one or more of the blood-based parameters that has priority status exceeds one or more of the predetermined threshold values, then an adverse physiological effect is determined. The predetermined threshold values may vary, e.g., from patient to patient, but may be selected such that the stimulation therapy process is configured to provide a closed-loop adjustment of the stimulation parameters based on blood parameter sensing to minimize or prevent the adverse physiological effect from reoccurring during the remainder of stimulation therapy.

Optionally, the adverse physiological effect may be determined based on a combination of the blood-based parameters. For example, in some embodiments, a composite predetermined threshold may be set that takes into consideration a combination of the blood-based parameters. If the combination of the blood-based parameters exceeds the composite predetermined threshold, then an adverse physiological effect is determined. In other embodiments, the blood-based parameters may be assigned weights, for example blood flow may be designated a greater weight than blood pressure. If the combination in the weighted blood-based parameters exceeds the composite predetermined threshold, then an adverse physiological effect is determined. The composite predetermined threshold may vary, e.g., from patient to patient, but may be selected such that the stimulation therapy process is configured to provide a closed-loop adjustment of the stimulation parameters based on blood parameter sensing to minimize or prevent the adverse physiological effect from reoccurring during the remainder of stimulation therapy.

In 515, one or more of the stimulation parameters is modified to bring the adverse physiological effect within acceptable levels. In various embodiments, one or more of the stimulation parameters is modified (e.g., using the one or more processors) based on the responses of the nerve or artery/nerve plexus and/or the blood-based parameters to create a modified set of stimulation parameters (e.g., a second set of stimulation parameters). In some embodiments, one or more of the burst duration, the burst interval, the stimulation amplitude, the pulse width, the frequency, the duty cycle, stimulation waveform shape, and the electrode configuration is changed to bring the adverse physiological effect within acceptable levels. The changes in the parameter settings may vary, but may be selected so that one or more of the parameters are set at levels below previously set levels, such that the adverse physiological effect is minimized or prevented from reoccurring during the remainder of stimulation therapy. In some embodiments, the burst duration, the burst interval, the frequency, and electrode configuration are maintained at target levels or configurations, while one or more of the stimulation amplitude, the pulse width, stimulation waveform shape, and the duty cycle are reduced below their respective previous levels. In other embodiments, the initial electrode configuration is maintained at a target level or configuration, while one or more of the burst duration, the burst interval, the frequency, the stimulation amplitude, the pulse width, stimulation waveform shape, and the duty cycle are reduced below their respective previous levels. In yet other embodiments, the burst duration, the burst interval, the frequency, the stimulation amplitude, the pulse width, stimulation waveform shape, and the duty cycle are maintained at target levels, while the electrode configuration is modified. Once the one or more of the stimulation parameters are modified, the process proceeds to 505, to deliver stimulation to the patient using the modified set of stimulation parameters and monitor nerve responses and the blood-based parameters to determine whether the stimulation provided using the modified set of stimulation parameters still has an adverse physiological effect on the patient.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

The invention claimed is:

1. A system comprising:
a neurostimulator configured to delivery stimulation for a nerve or artery/nerve plexus based on a first set of stimulation parameters;
one or more sensors configured to monitor a response to the stimulation that includes monitoring responses of the nerve or artery/nerve plexus; and
a controller configured to modify the first set of stimulation parameters based on the responses of the nerve or artery/nerve plexus to create a second set of stimulation parameters, wherein the controller is configured to modify the first set of stimulation parameters based on a titration schedule;
wherein the neurostimulator is further configured to deliver the stimulation based on the second set of the stimulation parameters, wherein the neurostimulator, the one or more sensors, and the controller are provided within a distributed environment, and wherein at least the neurostimulator and the controller are in communication via a wireless communication network.

2. The system of claim 1, wherein the stimulation parameters include at least one of stimulation amplitude, pulse width, frequency, duty cycle, stimulation waveform shape, and electrode configuration.

3. The system of claim 1, wherein monitoring a response to the stimulation includes monitoring the blood-based parameters including at least one of blood flow, blood pressure, and arterial distension.

4. The system of claim 3, wherein the blood-based parameters are measured using one or more sensors including at least one of: a blood flow sensor, a blood pressure sensor, and a distension sensor.

5. The system of claim 4, wherein the blood flow sensor is a Doppler sensor configured to measure blood velocity or an impedance sensor configured to detect changes in electrical impedance of blood.

6. The system of claim 4, wherein the blood pressure sensor is an impedance sensor configured to measure the blood pressure or a piezoresistive pressure sensor configured to measure the blood pressure.

7. The system of claim 4, wherein the distension sensor is a capacitive sensor configured to measure the arterial distension, a photonic sensor configured to measure arterial distension based on a change in amount of photons transmitted, or a Doppler sensor configured to measure cardiac motion and artery diameter pulsation.

8. The system of claim 3, wherein the modifying includes modifying the first set of stimulation parameters based on the blood-based parameters and the information regarding the electrical impulses to create the second set of stimulation parameters.

9. A system comprising:
an implantable neurostimulator including:
a controller configured to:
deliver neural stimulation using a pulse generator and one or more electrodes based on a first set of stimulation parameters to a nerve or artery/nerve plexus;
monitor a response to the neural stimulation that includes monitoring responses of the nerve or artery/nerve plexus, wherein monitoring the response to the neural stimulation includes determining whether the neural stimulation has a physiological effect;
modify the first set of stimulation parameters based on the monitored response to create a second set of stimulation parameters; and deliver the neural stimulation using the pulse generator and the one or more electrodes based on the second set of the stimulation parameters, wherein the controller is configured to modify the first set of stimulation parameters based on a titration schedule.

10. The system of claim 9, wherein determining whether the neural stimulation has a physiological effect includes obtaining the blood-based parameters and comparing the blood-based parameters to one or more predetermined thresholds to determine whether the neural stimulation has an adverse physiological effect on the blood-based parameters.

11. The system of claim 10, wherein when the neural stimulation has an adverse physiological effect, the operations further comprise modifying the first set of stimulation parameters based on the blood-based parameters to create the second set of stimulation parameters.

12. The system of claim 9, wherein the controller is configured to determine whether adequate adaptation is achieved, further wherein the adequate adaptation is achieved when at least one of the following objectives is achieved: acceptable levels for the blood-based parameters, a target intensity level for one or more of the stimulation parameters, and a target physiological effect.

13. The system of claim 9, wherein monitoring a response to the stimulation includes monitoring the blood-based parameters including at least one of blood flow, blood pressure, and arterial distension.

14. The system of claim 13, wherein the blood-based parameters are measured using one or more sensors including at least one of: a blood flow sensor, a blood pressure sensor, and a distension sensor.

15. The system of claim 14, wherein the blood flow sensor is a Doppler sensor configured to measure blood velocity or an impedance sensor configured to detect changes in electrical impedance of blood.

16. The system of claim 14, wherein the blood pressure sensor is an impedance sensor configured to measure the blood pressure or a piezoresistive pressure sensor configured to measure the blood pressure.

17. A method comprising:
delivering, by a computing system, neural stimulation to a nerve or artery/nerve plexus based on a first set of stimulation parameters;
monitoring, by the computing system, a response to the neural stimulation that includes monitoring whether the neural stimulation has a physiological effect or changes to blood-based parameters;
modifying, by the computing system, the first set of stimulation parameters based on a titration schedule and on the physiological effect or blood-based parameters to create a second set of stimulation parameters; and
delivering, by the computing system, the neural stimulation based on the second set of the stimulation parameters.

* * * * *